United States Patent
Miller

(10) Patent No.: US 9,498,449 B2
(45) Date of Patent: *Nov. 22, 2016

(54) METHODS OF FEEDING ANIMALS LIQUID FEED WITH SOLUBLE FIBER AND SUGAR ALCOHOL

(71) Applicant: PURINA ANIMAL NUTRITION LLC, Shoreview, MN (US)

(72) Inventor: Bill L. Miller, Labadie, MO (US)

(73) Assignee: PURINA ANIMAL NUTRITION LLC, Shoreview, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/990,011

(22) Filed: Jan. 7, 2016

(65) Prior Publication Data

US 2016/0113886 A1 Apr. 28, 2016

Related U.S. Application Data

(60) Continuation of application No. 14/720,227, filed on May 22, 2015, now Pat. No. 9,271,516, which is a continuation of application No. 12/100,694, filed on Apr. 10, 2008, now Pat. No. 9,044,040, which is a division of application No. 10/942,156, filed on Sep. 16, 2004, now Pat. No. 7,371,401.

(51) Int. Cl.
| | | |
|---|---|---|
| *A61K 31/047* | (2006.01) | |
| *A23K 1/18* | (2006.01) | |
| *A23K 1/16* | (2006.01) | |
| *A61K 36/18* | (2006.01) | |

(52) U.S. Cl.
CPC ........... *A61K 31/047* (2013.01); *A23K 1/1609* (2013.01); *A23K 1/1813* (2013.01); *A23K 1/1893* (2013.01); *A23K 10/30* (2016.05); *A23K 10/32* (2016.05); *A23K 20/163* (2016.05); *A61K 36/18* (2013.01); *Y10S 426/807* (2013.01)

(58) Field of Classification Search
None
See application file for complete search history.

(56) References Cited

U.S. PATENT DOCUMENTS

| | | |
|---|---|---|
| 4,598,097 A | 7/1986 | Perry et al. |
| 4,981,697 A | 1/1991 | Miller et al. |
| 5,009,899 A | 4/1991 | Miller et al. |
| 5,213,826 A | 5/1993 | Miller et al. |
| 5,503,112 A | 4/1996 | Luhman et al. |
| 5,571,542 A | 11/1996 | Miller et al. |
| RE35,699 E | 12/1997 | Lange et al. |
| 6,066,341 A | 5/2000 | Wilson |
| 6,156,333 A | 12/2000 | Langrehr |
| 6,348,223 B1 | 2/2002 | Claycamp et al. |
| 6,406,729 B1 | 6/2002 | Miller et al. |
| 6,440,447 B1 | 8/2002 | Luhman |
| 6,541,047 B1 | 4/2003 | Claycamp et al. |
| 6,866,861 B1 | 3/2005 | Luhman |
| 7,371,401 B2 * | 5/2008 | Miller ............ A23K 1/12 424/438 |
| 7,956,045 B2 | 6/2011 | Lane |
| 9,044,040 B2 * | 6/2015 | Miller ............ A23K 1/12 |
| 9,271,516 B2 * | 3/2016 | Miller ............ A23K 1/12 |
| 2003/0068390 A1 | 4/2003 | Miller et al. |
| 2003/0194424 A1 | 10/2003 | Lis et al. |

FOREIGN PATENT DOCUMENTS

WO  WO 96/32849  10/1996

OTHER PUBLICATIONS

McGill University; Calf Feeding and Man—Production, pp. 1-24, 1990.
Roquette, *Significance of Adding Neosorb Sorbitol to the Feed Ration of Calves and Young Bulls*, pp. 1-24, 1988.
Bauchart et al., *Addition of Sorbitol to a Milk Substitute for Veal Calves*, Reproduction Nutritional Development, 1985, 25(2), 339-410.
Farnam Companies, Inc., website, *One Day Response*, 2 pages, May 25, 2004.

* cited by examiner

*Primary Examiner* — Robert A Wax
*Assistant Examiner* — Melissa Mercier
(74) *Attorney, Agent, or Firm* — Dorsey & Whitney LLP; Bridget M. Hayden, Esq.

(57) ABSTRACT

An animal feed such as a milk replacer includes a soluble fiber and a sugar alcohol. The milk replacer enhances weight gain, starter intake and reduces weaning time. The method of feeding the animal includes feeding a mixture of a soluble fiber and sugar alcohol. The animal feed may be used as a method of weaning young ruminants such as calves.

20 Claims, No Drawings

METHODS OF FEEDING ANIMALS LIQUID FEED WITH SOLUBLE FIBER AND SUGAR ALCOHOL

CROSS-REFERENCE TO RELATED APPLICATIONS

This application is a continuation of U.S. application Ser. No. 14/720,227 filed May 22, 2015, issued as U.S. Pat. No. 9,271,516 on Mar. 1, 2016, which is a continuation of U.S. application Ser. No. 12/100,694 filed Apr. 10, 2008, issued as U.S. Pat. No. 9,044,040 on Jun. 2, 2015, which is a Divisional of U.S. application Ser. No. 10/942,156 filed Sep. 16, 2004, issued on May 13, 2008 as U.S. Pat. No. 7,371,401, the contents of each of which are herein incorporated by reference in their entirety.

BACKGROUND OF THE INVENTION

The present invention relates generally to a method of making an animal feed and in particular an improved milk replacer having a soluble fiber and a sugar alcohol.

Livestock are generally weaned prior to their ability to consume whole foods. In the case of dairy cattle, calves may be fed whole milk or a milk replacer until the calves are weaned and ready to consume solid food. Feeding calves milk replacer is generally preferred since the milk replacer not only mimics the milk in terms of protein, fat and carbohydrate content, but also may be fortified with vitamins, medication and other nutritional supplements which benefit the young calves. Furthermore, milk replacer is a powder that has been spray dried at high temperatures eliminating disease organisms that may have existed in the ingredients that comprise the milk replacer. The powder form of the milk replacer also provides for easy storage.

Young livestock such as calves, piglets, horses, sheep, goats and other ruminants are very susceptible to bacteria that cause scours (diarrhea). Scours can lead to dehydration of the young animal and many studies have been conducted that show when young animals have experienced scours, their growth and development is less than animals that have not experienced scours. Less growth and development, of course, results in less profitability for the farmer.

It has been suggested that adding psyllium to milk replacer may be effective in reducing scours in calves. Martin J. Fettman, *Potential Benefits of Psyllium Mycelioid Supplementation of Replacement Formulas for Neonatal Calf Scours*, North America, Ed., February 1992, at 247 (Fettman Article). The Fettman Article based its opinion upon the properties of psyllium as well as the effectiveness of psyllium in reducing intestinal disorders in other animals and humans.

The use of psyllium (plantago seed supplement) in animal feed is also disclosed in Van Magius, PCT Patent Application No. WO82/02650 (Van Magius Patent). The Van Magius Patent application describes using plantago seed supplement to reduce animal stress conditions, prevent or treat scours, and promote growth.

Further use of a stable suspension of psyllium and the calf milk replacer has been described in the Miller et al. U.S. Pat. Nos. 5,571,542 and 6,406,729. In addition, the use of sorbitol as a feed component for cows is described in the Luhman U.S. Pat. No. 6,440,447.

Weaning of young animals occurs when the liquid feed is withdrawn from the diet. Thus, as used herein, "pre-weaning period" refers to the period when nutrients are predominantly or entirely supplied in liquid form such as to a calf as part of a liquid feed, and "post-weaning period" refers to the period when nutrients are no longer predominantly or entirely provided to the calf in the form of liquid feed.

Typical liquid feeds for young animals include fluid milk or fluid milk replacers. In the case of dairy cows fluid milk replacers are frequently substituted in place of fluid milk because fluid milk that is produced by mature, lactating dairy cows is generally more valuable when sold to consumers or when used to manufacture food products that are sold to consumers. Thus, fluid milk replacers that are produced to simulate fluid milk are generally substituted in place of fluid milk for feeding young calves. Fluid milk replacers may be based upon dairy components and non-dairy components that are combined to provide nutrient and palatability characteristics approximating the nutrient and palatability characteristics of fluid milk. Milk replacers are typically marketed in powdered form to avoid the higher transportation and storage costs of distributing fluid milk replacer. Powdered milk replacers are mixed with water prior to use to form fluid milk replacers that are provided to the young calves. The formulation and feeding of fluid milk replacers is well-known in the art.

Ruminants, such as cattle, are commonly bred and raised to produce food products, such as milk and beef, for human consumption. Maturation of cattle, as evidenced by weight gain, is an important factor that helps determine when a cow is ready to produce milk or is ready for market. Dairy farmers and cattle ranchers are greatly interested in techniques for economically achieving enhanced rates of ruminant weight gain since such techniques beneficially reduce milk and beef production costs.

Also, dairy farmers and cattle ranchers recognize that the care and feeding of cattle both prior to weaning and after weaning play an important role in determining the amount and quality of products produced by the cattle. As an example, the age of dairy cows at freshening and the onset of lactation may be reduced by modifying the nutrient mix and nutrient composition in feed the dairy cows consume and by inducing the cows to gain weight more quickly during the pre-weaning and post-weaning periods prior to freshening. Also, in cattle ranching operations, increasing the rate of weight gain by young cattle beneficially reduces the time required for producing cattle with a size that is suitable for market.

In both dairy operations and ranching operations, it is also generally desirable to increase the feed efficiency of young ruminants. The greater the feed efficiency the less feed required by the ruminant to obtain a unit amount of weight gain.

A major overall desire of dairy farmers and ranchers alike is to reduce the overall cost to produce a product, such as milk or beef, with an acceptable level of quality. Depending upon numerous cost variables, such as the cost of feed, labor costs on the farm or ranch, and equipment and building costs on the farm or ranch, this desired cost reduction may be achieved by increasing the rate of weight gain by young ruminants and/or increasing the feed efficiency of young ruminants. Thus, dairy farmers and ranchers, depending upon their particular cost variables, may employ either enhanced rates of weight gain or increased feed efficiency or a combination of enhanced rates of weight gain and increased feed efficiency to reduce the cost of bringing milk and beef to the consumer market.

To complement liquid feeds that are fed to ruminants, such as cattle, prior to weaning, a number of additives and supplements have been developed for feeding calves along with the liquid feed during the pre-weaning period. These additives and supplements have been developed for a number of different purposes. For example, some additives and supplements have been developed to generally enhance the health of the young calves or help prevent or control development of specific conditions or ailments, such as scours. Additionally, some additives or supplements have been developed in an attempt to enhance appetite, enhance maturation rate, and/or enhance weight gain.

In this regard, various veterinary pharmaceutical compositions have been developed to help prevent or inhibit development of certain ailments in ruminants. Also, numerous vitamin compositions have been developed to help enhance the general health of ruminants and/or to help prevent or inhibit development of ailments or conditions in ruminants. Finally, the use of psyllium has been prescribed for reducing scours in calves. Also, psyllium incorporation in the diet of ruminants has been described for increasing the rate of weight gain per unit weight of protein that is consumed by ruminants.

Though the various ruminant feed supplements and additives that have been proposed and/or practiced over the years have enhanced the overall knowledge base with respect to ruminant feeding, these feed supplements and additives, as well as feeding techniques that employ these feed supplements and additives, have not yet been fully identified, addressed, or optimized options for increasing the rate of weight gain exhibited by ruminants or for increasing the feed efficiency of ruminants. Thus, dairy farmers and ranchers alike are still in need of new approaches to feeding ruminants that enhance weight gain rates in ruminants and/or increase the feed efficiency of ruminants.

SUMMARY OF THE INVENTION

The present invention includes an animal feed such as a milk replacer having a soluble fiber and a sugar alcohol and a method of making the same. The milk replacer enhances weight gain, starter intake and reduces weaning time. The present invention also includes a method of feeding an animal a mixture of a soluble fiber and a sugar alcohol. The present invention further includes a method of making an animal feed that includes a soluble fiber and a sugar alcohol. The present invention also includes a method of weaning a ruminant such as a calf by feeding the ruminant a soluble fiber and a sugar alcohol. The present invention also includes a calf milk replacer containing an effective amount of psyllium and a sugar alcohol for reducing weaning time.

DETAILED DESCRIPTION OF THE PREFERRED EMBODIMENTS

It has been found that an animal feed such as a calf milk replacer containing both a soluble fiber and a sugar alcohol enhances weight gain, starter intake, and reduces weaning time. In addition scour severity is also reduced. Calves fed an enhanced amount of milk replacer are especially benefited. Although the present invention has been found very suitable in weaning calves, the present invention is suitable for all livestock. By livestock is meant agricultural animals such as swine, horses and ruminants such as but not limited to cows, sheep and goats.

Psyllium is the preferred soluble fiber used in the present invention. By soluble fiber is meant that part of plant foods that cannot be digested or absorbed and that readily disperses in an aqueous solution. Soluble fibers may include gums, hydrocolloides, most pectins, mucilages and some hemicelluloses. Psyllium is a hemicellulose. Preferably the psyllium should be in the form of a powder with a fine particle size. The fine particle size helps to disperse and maintain the particles of psyllium in solution and helps to enhance the rate of water absorption and the amount of water absorbed by the psyllium. The psyllium is preferably fed at approximately 16 grams per day and preferably at least approximately 6 grams per day and up to approximately 19 grams per day. The use of psyllium above 19 grams per day may still have the effect of the present invention but usage above 19 grams per day is less effective.

In the specific embodiment described herein, the psyllium is fed to a calf as a component of a milk replacer. The milk replacer is fed at an enhanced rate to the calf. Preferably, the enhanced feeding rate for the milk replacer is at least about 1.5 pounds of the milk replacer per day based on the dry weight of the milk replacer during the pre-weaning period.

Sugar alcohols useful in the present invention include adonitol; allitol; altritol (D-altritol, L-altritol, and D,L altritol); arabinitol (D-arabinitol, L-arabinitol, and D,L arabinitol); dulcitol (a.k.a galactitol); erythritol; galaxitol; glucitol (D-glucitol, L-glucitol, and D,L glucitol); glycerol; iditol (D-iditol and L-iditol); inositol; isomalt; lactitol; maltitol; mannitol (D-mannitol, L-mannitol, and D,L mannitol); perseitol; ribitol; rhamnitol; sorbitol; threitol (D-threitol, L-threitol, and D,L threitol); and xylitol. These sugar alcohols may be provided in any combination. All such sugar alcohols in combination with psyllium have the effect of the present invention. Preferably sorbitol is used due to its relative low cost in relation to the other sugar alcohols. Sorbitol was preferably fed at a rate of approximately 5 to 6 grams per day along with the amounts of psyllium discussed previously. Sorbitol is consumed preferably at least approximately 3 grams per day to have an effect and up to approximately 8 grams per day. Amounts of sorbitol ten grams and over per day were found not to have the same effect as the present invention. Therefore, it is preferred for the animals to consume approximately less than 10 g per day.

The sugar alcohol(s) is fed to the calf as a component of the milk replacer. The milk replacer includes the animal feed of the present invention such as the milk replacer is made by adding the sugar alcohol into the dry milk replacer (containing psyllium). The milk replacer (now containing the sugar alcohol and psyllium) is then hydrated by the farmer or rancher for feeding to the calf.

The method of the present invention is described in the following example. This example is provided as an illustration of the invention and is not intended to limit the invention in any way.

Example

A total of 56 calves were provided with the milk replacer of the present invention in three separate trials. The sugar alcohol used in these trials was sorbitol. The calf milk replacer (CMR) used was Cow's Match® from Land O'Lakes, Inc of Arden Hills, Minn. Cow's Match® contains approximately 1.38% psyllium. The results from the three trials were combined and are set forth below in Tables 1 through 4. The procedures followed in all three trials were similar.

The calves used in the trials were approximately 3 to 10 days old at the trial's initiation. Each calf was weighed initially upon arrival and weekly thereafter. Other performance parameters were determined on a daily basis.

As Table 1 set forth below indicates, a significant gain in weight occurred in the calves in periods 1 and 2. These periods correspond to the first two weeks of the trials. In addition to the first two periods, the total weight gain for the seven periods for calves fed Cow's Match® with sorbitol showed approximately 7.9% greater increase over the calves not fed the sorbitol.

There was also a significantly greater starter intake by the calves fed Cow's Match® with sorbitol in periods 2 through 5. Total starter intake by calves fed Cow's Match® with sorbitol was 17.7% greater than calves not fed sorbitol. This was also statistically significant.

TABLE 1

| Item | | Cow's Match (CMR) | Cow's Match (CMR) w/ Sorbitol[A] | P-value | C.V. |
|---|---|---|---|---|---|
| | | 1 | 2 | | |
| No. of Calves | | 56 | 56 | | |
| Initial Wt., lbs. | | 104.85 | 104.46 | 0.6418 | 4.28 |
| Initial Ig[B] | | 3.75 | 3.91 | 0.4341 | 28.28 |
| Avg. Period Gain, lbs. | | | | | |
| Period[C] | 1 | 2.47 | 4.65 | 0.0085 | 121.09 |
| | 2 | 7.69 | 9.79 | 0.0418 | 61.61 |
| | 3 | 12.70 | 12.86 | 0.7933 | 25.34 |
| | 4 | 12.44 | 12.67 | 0.7075 | 26.02 |
| | 5 | 13.49 | 14.14 | 0.2317 | 20.70 |
| | 6 | 15.17 | 16.60 | 0.0188 | 20.01 |
| | 7 | 14.36 | 13.80 | 0.5754 | 37.56 |
| | Total | 78.32 | 84.51 | 0.0248 | 17.69 |
| Avg. Period CMR Consumption, lbs.[D] (DM Basis) | | | | | |
| Period | 1 | 10.46 | 10.77 | 0.2886 | 14.84 |
| | 2 | 15.10 | 15.91 | 0.0840 | 15.91 |
| | 3 | 16.82 | 16.88 | 0.7911 | 7.32 |
| | 4 | 17.39 | 17.32 | 0.5502 | 3.63 |
| | 5 | 17.42 | 17.39 | 0.8148 | 3.34 |
| | 6 | 17.45 | 17.49 | 0.1914 | 1.06 |
| | 7 | 8.75 | 8.74 | 0.3195 | 0.34 |
| | Total | 103.37 | 104.51 | 0.2209 | 4.70 |
| Avg. Period Starter Intake[E], lbs. (DM Basis) | | | | | |
| Period | 1 | 0.45 | 0.62 | 0.1941 | 123.58 |
| | 2 | 0.91 | 1.30 | 0.0131 | 75.27 |
| | 3 | 1.65 | 2.27 | 0.0122 | 65.84 |
| | 4 | 2.81 | 3.71 | 0.0102 | 56.06 |
| | 5 | 4.16 | 5.30 | 0.0107 | 48.79 |
| | 6 | 6.74 | 7.99 | 0.0519 | 45.43 |
| | 7 | 15.02 | 16.17 | 0.2619 | 34.64 |
| | Total | 31.74 | 37.35 | 0.0283 | 38.65 |
| Average Feed: Gain[F] | | 1.75 | 1.71 | 0.2844 | 10.57 |

[A]From Neosorb 70/20 (70% active ingredient sorbitol) Roquette America, Gurnee, IL.
[B]Gram - % as measured by Zinc Sulfate Turbidity and assigned to 1 of 5 ranges: 0.00-0.49, 0.50-0.99, 1.00-1.49, 1.50-2.49, and 2.50 or higher.
[C]Seven day duration.
[D]Calves were fed 0.9 lbs. CMR/feeding days 1-7, then 1.25 lbs. CMR/feeding days 7-49. CMR twice a day through day 42, then once a day through day 49.
[E]Intense Calf Diet 22 B60, 60 g/ton lasalocid (Land O'Lakes, Inc., Arden Hills, MN).
[F]Average feed: gain is the amount of feed intake divided by the weight gain of each individual calf. The individual values summed and then averaged.
Bold face type indicates a difference of P < 0.05.

The calves fed Cow's Match® with sorbitol showed a significant decrease in period 1 in severity of scours (scour score), and the number of scour days experienced. Data was grouped and considered for the first two weeks (first two periods) since scouring is most prevalent in the first two weeks. Scour severity was significantly reduced in the first two weeks for the calves consuming psyllium with sorbitol as compared to the calves not being fed sorbitol.

TABLE 2

| Item | | Cow's Match (CMR) | Cow's Match (CMR) w/ Sorbitol[A] | P-value | C.V. |
|---|---|---|---|---|---|
| | | 1 | 2 | | |
| Avg. Period Scour Score[B] | | | | | |
| Period[C] | 1 | 1.86 | 1.61 | 0.0021 | 24.26 |
| | 2 | 1.61 | 1.56 | 0.5583 | 27.61 |
| | 3 | 1.10 | 1.09 | 0.7919 | 18.63 |
| | 4 | 1.05 | 1.04 | 0.6900 | 11.29 |
| | 5 | 1.02 | 1.04 | 0.1732 | 8.63 |
| | 6 | 1.00 | 1.00 | 0.0000 | 0.00* |
| | 7 | 1.00 | 1.01 | 0.1563 | 1.89 |
| Avg. 2 wk | | 1.73 | 1.58 | 0.0286 | 21.51 |
| Avg. 7 wk | | 1.23 | 1.19 | 0.0919 | 10.63 |
| Avg. Period Scour Days[D] | | | | | |
| Period | 1 | 4.43 | 3.25 | 0.0018 | 50.67 |
| | 2 | 3.41 | 3.30 | 0.8030 | 67.53 |
| | 3 | 0.66 | 0.61 | 0.8305 | 208.36 |
| | 4 | 0.36 | 0.29 | 0.6420 | 252.20 |
| | 5 | 0.11 | 0.27 | 0.1732 | 330.88 |
| | 6 | 0.00 | 0.00 | 0.0000 | 0.00* |
| | 7 | 0.00 | 0.04 | 0.1563 | 741.50 |
| Total 2 wk | | 7.84 | 6.55 | 0.0515 | 48.02 |
| Total 7 wk | | 8.96 | 7.75 | 0.1764 | 56.50 |

[A]From Neosorb 70/20 (70% active ingredient sorbitol) Roquette America, Gurnee, IL.
[B]Scour Score = 1-4 scale; 1 = normal, 2-loose, 3 = water separation, 4 = 3 with severe dehydration.
[C]Seven day duration.
[D]Total days with a scour score of 2 or greater
*No differences due to no variations within treatments.
Bold face type indicates a difference of P < 0.05.

Although not significantly different, the calves fed sorbitol with psyllium as indicated in Table 3 below had a 15.9 percent improvement in respiratory score compared with calves not fed sorbitol but only psyllium.

TABLE 3

| Item | | Cow's Match (CMR) | Cow's Match (CMR) w/ Sorbitol[A] | P-value | C.V. |
|---|---|---|---|---|---|
| | | 1 | 2 | | |
| Avg. Period Respiratory Scores[B] | | | | | |
| Period[C] | 1 | 0.36 | 0.14 | 0.2119 | 361.24 |
| | 2 | 1.50 | 1.13 | 0.3288 | 154.12 |
| | 3 | 1.45 | 1.07 | 0.3263 | 159.86 |
| | 4 | 1.27 | 1.23 | 0.9260 | 162.34 |
| | 5 | 1.54 | 1.29 | 0.5551 | 158.41 |
| | 6 | 0.71 | 0.54 | 0.4948 | 220.73 |
| | 7 | 0.36 | 0.64 | 0.3100 | 296.47 |
| Total | | 7.18 | 6.04 | 0.3215 | 91.91 |

[A]From Neosorb 70/20 (70% active ingredient sorbitol) Roquette America, Gurnee, IL.
[B]Respiratory scores = 1 respiratory day for each day antibiotic given for respiratory infections.
[C]Seven day duration.

As indicated in Table 4 below, a statistically significant greater amount of calves fed sorbitol with psyllium were weaned by day 28. Specifically, five times as many of these calves could have been weaned by day 28 employing the LOL Research Farm criteria as indicated in row 1 of Table 4.

TABLE 4

| Item | | Cow's Match | Cow's Match w/Sorbitol[A] | P-value | C.V. |
|---|---|---|---|---|---|
| | | 1 | 2 | | |
| Avg. Period Weaning Scores[B] | | | | | |
| LOLRF[C] | 28[F] | 4 | 20 | 0.0076 | 269.55 |
| | 35[G] | 25 | 38 | 0.1563 | 148.30 |
| | 42[H] | 63 | 77 | 0.1019 | 65.81 |
| | 49[I] | 98 | 98 | 1.0000 | 13.61 |
| IC[D] | 28 | 0 | 4 | 0.1563 | 741.50 |
| | 35 | 5 | 9 | 0.4676 | 362.94 |
| | 42 | 20 | 38 | 0.0367 | 156.40 |
| | 49 | 91 | 95 | 0.4676 | 27.92 |

[A]From Neosorb 70/20 (70% active ingredient sorbitol) Roquette America, Gurnee, IL.
[B]Weaning Scores = 0-1 scale; 0 = not weaned, 1 = weaned.
[C]Land O' Lakes Research Farm Criteria = calf assumed weaned when 1.0 lb of dry feed consumed for 2 consecutive days.
[D]Industry Criteria = calf assumed weaned when 1.5 lbs dry feed consumed for 3 consecutive days.
[F]Percentage of calves assumed weaned by day 28.
[G]Percentage of calves assumed weaned by day 35.
[H]Percentage of calves assumed weaned by day 42.
[I]Percentage of calves assumed weaned by day 49.
Bold face type indicates a difference of $P < 0.05$.

A further trial was ran to determine what effect sorbitol without a dietary fiber would have on calves fed an intensified diet of calf milk replacer. Forty-six three to ten day old Holstein bull calves weighing approximately 90 to 100 pounds were fed an intensified diet of calf milk replacer. Twenty-four calves were fed a calf milk replacer without psyllium and without sorbitol and twenty-two calves were fed calf milk replacer without psyllium but with sorbitol. The latter 24 calves were fed 6 grams each per day of sorbitol.

As Table 5 set forth below shows, there was no statistically significant difference in total weight gain, calf milk replacer consumption, starter feed intake and average feed:gain (feed efficiency) between those calves fed no sorbitol and those calves fed 6 g per day of sorbitol.

TABLE 5

| Item | | Cow's Match (CMR) | Cow's Match (CMR) With 6.0 g Sorbitol[A] | P-value | C.V. |
|---|---|---|---|---|---|
| | | 1 | 2 | | |
| Treatments | | | | | |
| No. of Calves | | 24 | 22 | | |
| Initial Weight, lbs. | | 107.51 | 107.63 | 0.8953 | 2.94 |
| Initial Ig[B] | | 3.13 | 3.00 | 0.6949 | 34.99 |
| Avg. Period Gain, lbs. | | | | | |
| Period[C] | 1 | 1.27 | 2.96 | 0.2049 | 214.98 |
| | 2 | 9.23 | 9.28 | 0.9645 | 42.79 |
| | 3 | 12.70 | 11.40 | 0.2602 | 31.97 |
| | 4 | 12.62 | 12.78 | 0.8840 | 29.28 |
| | 5 | 13.82 | 13.28 | 0.5484 | 22.09 |
| | 6 | 14.72 | 14.34 | 0.5902 | 16.34 |
| | 7 | 12.22 | 12.55 | 0.8093 | 37.61 |
| | Total | 76.57 | 76.60 | 0.9951 | 20.54 |
| Avg. Period CMR Consumption, lbs.[D] (DM Basis) | | | | | |
| Period | 1 | 10.55 | 10.69 | 0.8012 | 16.65 |
| | 2 | 14.28 | 14.47 | 0.7771 | 16.18 |
| | 3 | 16.77 | 15.94 | 0.1509 | 11.72 |
| | 4 | 17.18 | 16.48 | 0.2019 | 10.88 |
| | 5 | 17.20 | 17.09 | 0.7147 | 5.88 |
| | 6 | 17.39 | 17.24 | 0.4526 | 3.69 |
| | 7 | 8.75 | 8.75 | 0.0000 | 0.00* |
| | Total | 102.11 | 100.65 | 0.4807 | 6.83 |
| Avg. Period Starter Intake[E], lbs. (DM Basis) | | | | | |
| Period | 1 | 0.47 | 0.50 | 0.8387 | 98.31 |
| | 2 | 1.19 | 1.08 | 0.6588 | 72.16 |
| | 3 | 2.14 | 1.95 | 0.5577 | 53.11 |
| | 4 | 3.44 | 3.14 | 0.5409 | 51.31 |
| | 5 | 4.86 | 4.56 | 0.6475 | 46.82 |
| | 6 | 6.90 | 6.80 | 0.9175 | 46.33 |
| | 7 | 14.27 | 15.08 | 0.5922 | 34.49 |
| | Total | 33.28 | 33.11 | 0.9653 | 39.43 |
| Average Feed: Gain | | 1.80 | 1.79 | 0.8771 | 12.31 |

[A]From Neosorb 70/20 (70% active ingredient sorbitol) Roquette America, Gurnee, IL.
[B]Gram - % as measured by Zinc Sulfate Turbidity and assigned to 1 of 5 ranges: 0.00-0.49, 0.50-0.99, 1.00-1.49, 1.50-2.49, and 2.50 or higher.
[C]Seven day duration.
[D]Calves were fed 0.9 lbs. CMR/feeding days 1-7, then 1.25 lbs. CMR/feeding days 7-49. CMR was fed twice a day through day 42, then once a day through day 49.
[E]Intense Calf Diet 22 B60, 60 grams per ton lasalocid, (Willmar, MN).
*No differences, due to no variation within treatments.

As Table 6 indicates, there was no statistically significant different between the scour score or scoured days for those calves fed 6 g of sorbitol per day and those calves fed with no sorbitol.

TABLE 6

| Item | | Cow's Match (CMR) | Cow's Match (CMR) With 6.0 g Sorbitol[A] | P-value | C.V. |
|---|---|---|---|---|---|
| Treatments | | 1 | 2 | | |
| Avg. Period Scour Score[B] | | | | | |
| Period[C] | 1 | 1.80 | 1.83 | 0.7396 | 16.95 |
| | 2 | 1.45 | 1.53 | 0.3471 | 19.90 |
| | 3 | 1.10 | 1.09 | 0.6891 | 13.33 |
| | 4 | 1.09 | 1.05 | 0.4408 | 15.16 |
| | 5 | 1.00 | 1.03 | 0.3015 | 8.29 |
| | 6 | 1.00 | 1.00 | 0.0000 | 0.00* |
| | 7 | 1.00 | 1.00 | 0.0000 | 0.00* |
| Avg. 2 wk | | 1.62 | 1.68 | 0.3905 | 13.43 |
| Avg. 7 wk | | 1.20 | 1.22 | 0.6240 | 6.87 |
| Avg. Period Scour Days[D] | | | | | |
| Period | 1 | 4.71 | 4.91 | 0.6703 | 33.03 |
| | 2 | 2.96 | 3.32 | 0.4975 | 56.93 |
| | 3 | 0.67 | 0.55 | 0.6860 | 165.75 |
| | 4 | 0.63 | 0.36 | 0.4396 | 227.07 |
| | 5 | 0.00 | 0.18 | 0.3015 | 677.53 |
| | 6 | 0.00 | 0.00 | 0.0000 | 0.00* |
| | 7 | 0.00 | 0.00 | 0.0000 | 0.00* |
| Total 2 wk | | 7.67 | 8.23 | 0.4596 | 32.09 |
| Total 7 wk | | 8.96 | 9.32 | 0.7289 | 38.29 |

[A]From Neosorb 70/20 (70% active ingredient sorbitol) Roquette America, Gurnee, IL.
[B]Scour Score = 1-4 scale; 1 = normal, 2 = loose, 3 = water separation, 4 = 3 with severe dehydration.
[C]Seven day duration.
[D]Total days with a scour score of 2 or greater
*No differences, due to no variation within treatments.

As Table 7 and 8 set forth below indicate, there was no statistically significant difference between respiratory scores and weaning scores for those calves fed 6 g per day of sorbitol and those calves not fed any sorbitol.

TABLE 7

| Item | | Cow's Match (CMR) | Cow's Match (CMR) With 6.0 g Sorbitol[A] | P-value | C.V. |
|---|---|---|---|---|---|
| Treatments | | 1 | 2 | | |
| Avg. Period Respiratory Scores[B] | | | | | |
| Period[C] | 1 | 0.92 | 1.05 | 0.8227 | 197.83 |
| | 2 | 1.00 | 1.05 | 0.9381 | 192.92 |
| | 3 | 1.04 | 1.82 | 0.2171 | 148.69 |
| | 4 | 2.42 | 1.82 | 0.4284 | 119.06 |
| | 5 | 1.17 | 0.77 | 0.4367 | 173.80 |
| | 6 | 0.25 | 0.77 | 0.2180 | 283.43 |
| | 7 | 0.21 | 0.00 | 0.3440 | 678.88 |
| Total | | 7.00 | 7.27 | 0.8851 | 89.16 |

[A]From Neosorb 70/20 (70% active ingredient sorbitol) Roquette America, Gurnee, IL.
[B]Respiratory scores = 1 respiratory day for each day antibiotic given for respiratory infections.
[C]Seven day duration.

TABLE 8

| Item | | Cow's Match (CMR) | Cow's Match (CMR) With 6.0 g Sorbitol[A] | P-value | C.V. |
|---|---|---|---|---|---|
| Treatments | | 1 | 2 | | |
| Avg. Period Weaning Scores[B] | | | | | |
| LOLRF[C] | 28[E] | 25 | 5 | 0.0554 | 231.37 |
| | 35[F] | 46 | 32 | 0.3416 | 126.21 |
| | 42[G] | 54 | 73 | 0.2009 | 76.83 |
| | 49[H] | 100 | 100 | 0.0000 | 0.00* |
| IC[D] | 28 | 0 | 0 | 0.0000 | 0.00* |
| | 35 | 0 | 5 | 0.3015 | 677.53 |
| | 42 | 29 | 27 | 0.8898 | 162.87 |
| | 49 | 83 | 91 | 0.4572 | 39.35 |

[A]From Neosorb 70/20 (70% active ingredient sorbitol) Roquette America, Gurnee, IL.
[B]Weaning Scores = 0-1 scale; 0 = not weaned, 1 = weaned.
[C]Land O' Lakes Research Farm Criteria = calf assumed weaned when 1.0 lb of dry feed consumed for 2 consecutive days.
[D]Industry Criteria = calf assumed weaned when 1.5 lbs dry feed consumed for 3 consecutive days.
[E]Percentage of calves assumed weaned by day 28.
[F]Percentage of calves assumed weaned by day 35.
[G]Percentage of calves assumed weaned by day 42.
[H]Percentage of calves assumed weaned by day 49.
*No differences, due to no variation within treatments.

Data for parameters presented in the Tables above was analyzed using the general linear model (GLM) statistical procedure of SAS™. Statistical analysis software for a randomized complete block design that included both the particular feed regimen and the week of the test period in the model statement. The SAS™ statistical analysis software is available from SAS Institute, Inc. of Cary, N.C. Additionally, all data was analyzed to determine the mean of the data for each variable under consideration during the collection period for the particular data.

Additionally, the PDiff function of the GLM statistical procedure was used to characterize the mean values of the data by providing for comparisons between mean data values for the calves of different treatments for particular test parameters or variables.

P used in the Tables above is a probability value. For purposes of comparing data in this document, P values of 0.10, or lower, are considered to be statistically significant. Thus, where a P value of 0.10 or less is returned for a particular variable, it is assumed that the differing results are fully explained by the test regimen, i.e. the presence or lack of sorbitol.

Also, the Tables include a coefficient of variation (CV) for data in a particular row. The coefficient of variation is the standard deviation of a particular variable divided by the mean of the variable and then multiplied by 100.

Although the present invention has been described with reference to preferred embodiments, workers skilled in the art will recognize that changes may be made in form and detail without departing from the spirit and scope of the invention.

What is claimed is:

1. A method of feeding a young livestock animal, the method comprising:
   feeding the young animal a soluble plant fiber and sorbitol dispersed in an aqueous solution and a starter feed,
   wherein in response to ingesting the aqueous solution and the starter feed, the animal increases a rate of weight gain.

2. The method of claim 1 wherein the animal consumes at least about 3 grams and up to 6 grams of the sorbitol per day.

3. The method of claim 1 wherein the animal consumes at least approximately 6 grams of the soluble plant fiber per day.

4. The method of claim 1 wherein the animal consumes up to approximately 16 grams of the soluble plant fiber per day.

5. The method of claim 1 wherein the young animal is a ruminant, a piglet, or a foal.

6. The method of claim 5 wherein the ruminant is a calf.

7. The method of claim 1 wherein the aqueous solution comprises a milk replacer.

8. A method of feeding a young livestock animal, comprising:
   feeding the animal a milk replacer comprising a soluble plant fiber from at least approximately 0.53 percent of the milk replacer on a dry weight basis and sorbitol,
   wherein the animal consumes at least about 3 grams and up to 6 grams of sorbitol per day.

9. The method of claim 8 wherein the sorbitol is from approximately 0.26 percent of the milk replacer on a dry weight basis.

10. The method of claim 8 wherein the sorbitol is up to approximately 1.76 percent of the milk replacer on a dry weight basis.

11. The method of claim 8 wherein the soluble plant fiber is up to approximately 3.35 percent of the milk replacer on a dry weight basis.

12. The method of claim 8 wherein the milk replacer comprises protein, fat and carbohydrates in an amount that mimics milk.

13. The method of claim 8 wherein the milk replacer is fed to the animal at about 1.25 pounds to about 2.5 pounds per day on a dry weight basis.

14. The method of claim 8 wherein the soluble plant fiber is a powdered soluble plant fiber.

15. The method of claim 8 wherein the animal ingests up to about 5 grams of the sorbitol on a dry weight basis.

16. A method of feeding an animal, comprising:
   feeding the animal a daily ration of a milk replacer, wherein the milk replacer comprises soluble plant fiber and sorbitol,
   wherein the animal consuming the milk replacer ingests at least approximately 6 grams of the soluble plant fiber and up to 6 grams of the sorbitol per day.

17. The method of claim 16, wherein the animal ingests at least about 3 grams of the sorbitol per day.

18. The method of claim 16, wherein the animal ingests up to about 19 grams of the soluble plant fiber per day.

19. The method of claim 16, wherein the soluble plant fiber comprises a powdered soluble plant fiber.

20. The method of claim 16, wherein the animal ingests up to about 5 grams of the sorbitol per day.

* * * * *